US010119903B2

(12) United States Patent
Arieli et al.

(10) Patent No.: US 10,119,903 B2
(45) Date of Patent: Nov. 6, 2018

(54) INTERFEROMETRIC ELLIPSOMETRY AND METHOD USING CONICAL REFRACTION

(71) Applicant: ADOM, Advanced Optical Technologies Ltd, Lod (IL)

(72) Inventors: Yoel Arieli, Jerusalem (IL); Yoel Cohen, Nes Ziona (IL)

(73) Assignee: ADOM, Advanced Optical Technologies Ltd., Lod (IL)

( * ) Notice: Subject to any disclaimer, the term of this patent is extended or adjusted under 35 U.S.C. 154(b) by 0 days.

(21) Appl. No.: 15/991,197

(22) Filed: May 29, 2018

(65) Prior Publication Data

US 2018/0275047 A1    Sep. 27, 2018

Related U.S. Application Data

(63) Continuation of application No. 15/113,161, filed as application No. PCT/IL2015/050077 on Jan. 22, 2015.

(Continued)

(51) Int. Cl.
*G01N 21/21* (2006.01)
*G01B 9/02* (2006.01)
*G01N 21/45* (2006.01)

(52) U.S. Cl.
CPC ....... *G01N 21/211* (2013.01); *G01B 9/02091* (2013.01); *G01N 21/45* (2013.01);
(Continued)

(58) Field of Classification Search
CPC ............... G01N 21/211; G01N 21/45; G01N 2201/06113; G01N 2290/70;
(Continued)

(56) References Cited

U.S. PATENT DOCUMENTS 3,985,447 A    10/1976 Aspnes
7,456,962 B2   11/2008 Blum
(Continued)

FOREIGN PATENT DOCUMENTS

WO    2013088106    6/2013

OTHER PUBLICATIONS

Notice of Allowance for U.S. Appl. No. 15/113,161 dated Mar. 1, 2018.
(Continued)

*Primary Examiner* — Michael P Lapage
(74) *Attorney, Agent, or Firm* — Workman Nydegger

(57) ABSTRACT

An apparatus and method for determining optical properties of an object includes a tunable monochromatic light source and an optical system for illuminating at least one point of the object with light from the light source, and collecting light reflected from the object. A biaxial birefringent crystal intercepts a beam of light reflected from the object and propagates the beam along an optical axis of the crystal and transforms the beam of reflected light to a ring of light having a periphery, each point of which has a different polarization plane. A detector array detects respective points along the periphery of the ring and a processing unit is coupled to the detector and is responsive to signals thereby for determining optical properties of the object.

12 Claims, 3 Drawing Sheets

Related U.S. Application Data

(60) Provisional application No. 61/931,626, filed on Jan. 26, 2014, provisional application No. 61/948,116, filed on Mar. 5, 2014.

(52) U.S. Cl.
CPC .... *G01B 2290/70* (2013.01); *G01N 2021/213* (2013.01); *G01N 2021/458* (2013.01); *G01N 2201/06113* (2013.01)

(58) Field of Classification Search
CPC ....... G01N 2021/458; G01N 2021/213; G01B 9/02091; G01B 2290/70
See application file for complete search history.

(56) References Cited

U.S. PATENT DOCUMENTS

| | | | | |
|---|---|---|---|---|
| 2003/0030817 A1* | 2/2003 | Lee | ........................ | G01B 11/00 356/491 |
| 2003/0090673 A1* | 5/2003 | Han | .................... | G01B 9/02056 356/491 |
| 2003/0220749 A1 | 11/2003 | Chen | | |
| 2006/0061768 A1* | 3/2006 | Duplain | ................. | G01D 5/266 356/479 |
| 2006/0103844 A1* | 5/2006 | Opsal | ........................ | G01J 4/04 356/369 |
| 2006/0193044 A1* | 8/2006 | Blum | ........................ | G01J 4/04 359/485.01 |
| 2009/0316157 A1* | 12/2009 | Saraf | ...................... | C25D 21/12 356/450 |
| 2013/0176574 A1* | 7/2013 | Sirat | .................. | G02B 21/0056 356/496 |
| 2014/0192364 A1* | 7/2014 | Yatagai | .................. | A61B 3/102 356/491 |

OTHER PUBLICATIONS

Non-Final Office Action for U.S. Appl. No. 15/113,161 dated Sep. 26, 2017.

Alba Peinado et al: "Conical refraction as a tool for polarization metrology", Optics Letters, Optical Society of America, US, vol. 38, No. 20, Oct. 15, 2013 (Oct. 15, 2013), pp. 4100-4103.

Angelo Pierangelo et al: "Ex-vivo characterization of human colon cancer by Mueller polarimetric imaging", Optics Express, vol. 19, No. 2, Jan. 17, 2011 (Jan. 17, 2011), pp. 1582-1593.

Lizana A et al: "Paper, Enhanced sensitivity to dielectric function and thickness of absorbing thin films by combining total internal reflection ellipsometry with standard ellipsometry and reflectometry; Enhanced sensitivity to dielectric function and thickness of absorbing thin films by combining total internal refle", Journal of Physics D: Applied Physics, Institute of Phsycis Publishing Ltd, GB, vol. 46, No. 10, Feb. 8, 2013 (Feb. 8, 2013) p. 105501.

International Search Report and Written Opinion for application No. PCT/IL2015/050077 dated Feb. 7, 2015.

* cited by examiner

INTERFEROMETRIC ELLIPSOMETRY AND METHOD USING CONICAL REFRACTION

CROSS-REFERENCES TO RELATED APPLICATIONS

The present invention is a Continuation of U.S. patent application Ser. No. 15/113,161 (published as US 2017/0023464), filed Jul. 21, 2016, which is incorporated herein by reference and which is a US national phase of PCT Application No. PCT IL/2015/050077 (published as WO 2015/111053), filed Jan. 22, 2015, which claims the benefit of the following US provisional patent applications:
U.S. Provisional Application 61/931,626, filed Jan. 26, 2014, and
U.S. Provisional Application 61/948,116, filed Mar. 5, 2014.

FIELD OF THE INVENTION

This invention relates to the use of conical refraction (CR) at a biaxial crystal for taking multi-polarizations ellipsometric measurements.

BACKGROUND OF THE INVENTION

Conical Refraction

When a focused input Gaussian beam propagates along the optic axis of a biaxial crystal, it is transformed into a light ring, as shown in FIG. 1. The radius of the CR ring depends on the crystal's length and its principal refractive indices.

One feature of the CR effect is that each point of the light ring is linearly polarized, with the polarization plane rotating along the ring so that every pair of diagonally opposite points has orthogonal polarizations. The biaxial crystal projects an input non-polarized beam into an infinite number of linearly polarized states.

Ellipsometry

Ellipsometry is an optical method for measuring a sample's properties such as thickness, complex refractive index or dielectric function tensor. The change of polarization of light upon transmission or reflection of the sample is measured and the sample's properties are calculated by comparing the results to a model. Typically, ellipsometry is done in the reflection mode. Since the ellipsometry exploits also phase information, very high resolution can be achieved.

Ellipsometry measures the complex reflectance ratio, rho, of the system:

$$\rho = \frac{r_p}{r_s} = \tan(\Psi)e^{i\Delta}$$

where $r_s$ and $r_p$ are the normalized amplitudes of the s and p polarizations, after reflection from the sample. Rho may also be parameterized by the amplitude component psi and the phase difference delta.

In general, the angle of incidence is chosen to be close to the Brewster angle of the sample to ensure a maximal difference in $r_p$ and $r_s$.

A typical apparatus for ellipsometric measurement is shown in FIG. 2. In the measurement process, the electromagnetic radiation emitted by a light source is linearly polarized by a polarizer. The linearly polarized light passes through an optional compensator (retarder, quarter wave plate) and illuminates the sample. After reflection, the radiation passes through a second optional compensator and an analyzer, and falls onto a detector.

Two common ellipsometers are based on rotating the polarizer or the analyzer. For the rotating polarizer configuration, the polarization state of light on the polarization generation arm of the instrument is modulated by rotating the polarizer continuously during measurement at a constant angular frequency while the compensator angle and the analyzer angle are fixed. For the rotating analyzer configuration, the analyzer on the polarization detection arm is rotated continuously, while the polarizer angle and compensator settings (if available) are fixed.

Since in general, the measured psi and delta cannot be converted directly into the optical constants of the sample, a model analysis must be performed. Using an iterative procedure (least-squares minimization) unknown optical constants and/or thickness parameters are varied, and psi and delta values are calculated using the Fresnel equations. The calculated psi and delta values which best match the experimental data provide the optical constants and thickness parameters of the sample.

Single-wavelength ellipsometry employs a monochromatic light source. However, using a monochromatic light source restricts the results to one set of psi and delta values per measurement. Spectroscopic ellipsometry (SE) employs broad band light sources, which cover a certain spectral range in the infrared, visible or ultraviolet spectral region. By that the complex refractive index or the dielectric function tensor in the corresponding spectral region can be obtained, which gives access to a large number of fundamental physical properties. In spectroscopic ellipsometry, a white light source along with a monochromator of some sort is used. In some cases, the monochromator is positioned prior to the polarizer and in some cases, after the analyzer.

The complex reflectance ratio, rho can also be attained by measuring the two complex amplitude of light reflected by the object for the two normal polarizations and dividing one complex amplitude of one polarization by the second complex amplitude of the normal polarization.

For very fast ellipsometric measurements the time needed for rotating the polarizer or the analyzer can be crucial.

There is thus required a method and system that allows parallel measurements and avoids the need for rotating the polarizer or the analyzer.

SUMMARY OF THE INVENTION

It is therefore an object of the present invention to provide a method and system that allows parallel measurements at an instant time and avoids the need for rotating the polarizer or the analyzer.

This object is realized in accordance with the invention by an apparatus and method for determining optical properties of an object having the features of the respective independent claims.

What is common to all embodiments is the use of a biaxial birefringent crystal for intercepting light reflected from an object and for propagating the light along an optical axis of the crystal and transforming the reflected light to a ring of light, each point of whose periphery has a different polarization plane. Typically, the polarization plane rotates between each pair of successive points along the periphery. Use of the biaxial birefringent crystal thus avoids the need to use a rotating polarizer or analyzer.

According to one embodiment of the present invention a biaxial crystal is used in conjunction with an ellipsometer for creating a ring of light with polarization plane rotating along the ring.

According to another embodiment of the present invention a dispersive biaxial crystal is used in conjunction with a multi-wavelength ellipsometer for creating different rings of light for each different wavelength with respective coaxial polarization planes rotating along each ring. This configuration also avoids the need for a spectrometer.

According to another embodiment of the present invention a biaxial crystal is used in conjunction with a multi-wavelength ellipsometer and a modulated light source for creating a ring of light with polarization plane rotating along the ring. This configuration also avoids the need for a spectrometer.

According to another embodiment of the present invention a biaxial crystal is used in conjunction with a multi-wavelength interferometer and a modulated light source for creating a ring of light with polarization plane rotating along the ring. This configuration also avoids the need for a spectrometer.

BRIEF DESCRIPTION OF THE DRAWINGS

In order to understand the invention and to see how it may be carried out in practice, embodiments will now be described, by way of non-limiting example only, with reference to the accompanying drawing, in which.

DETAILED DESCRIPTION OF INVENTION

Figure 1:
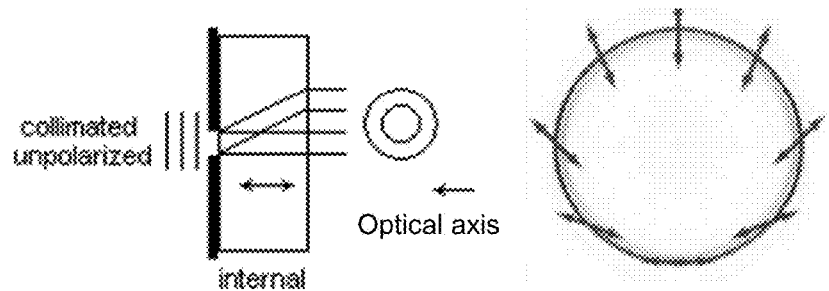
FIG. 1 shows schematically conventional conical refraction creating a light ring consists of light with different linear polarizations.
Figure 2:
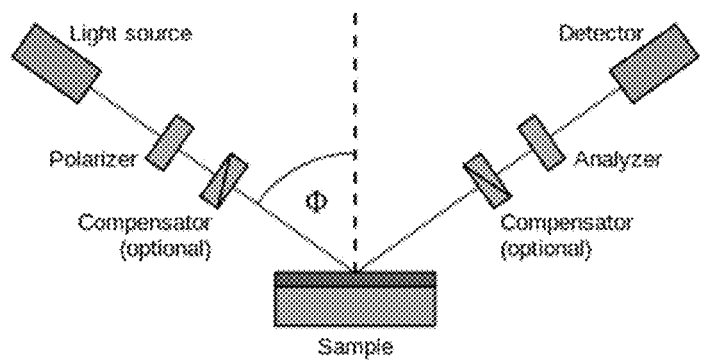
FIG. 2 shows schematically a conventional prior art apparatus for ellipsometric measurement.
Figure 3:
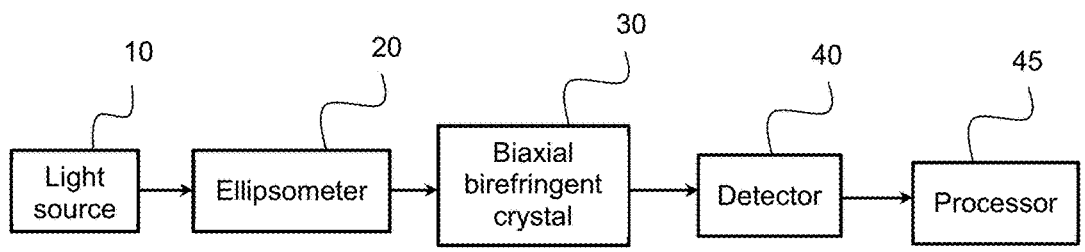
FIG. 3 shows schematically use of a biaxial crystal in conjunction with an ellipsometer according to one embodiment of the present invention.

FIG. 3 shows one embodiment of the present invention in which a biaxial crystal 30 is combined with an ellipsometer 20, constituting an optical system. The light source 10 of the ellipsometer may be a monochromatic light source. In this configuration, the analyzer in the ellipsometer is removed and the light reflected from the object is focused and it propagates along the optical axis of a biaxial birefringent crystal 30. The biaxial birefringent crystal propagates the reflected light and transforms in into a ring of light, such that each point along the periphery of the light ring is linearly polarized and whose polarization plane rotates along the ring. The ring of light is imaged either by propagation or by an optical system on to a detector array 40, which could be a CCD camera for example, to which there is coupled a processor 45 that processes the pattern imaged by the detector array 40 for obtaining an output indicating the object's optical properties. Since the polarization plane of each point along the ring is rotated, each point of the periphery has a different polarization plane and use of the biaxial birefringent crystal is equivalent to rotating an analyzer, and thus obviates the need for the rotating analyzer as is conventionally used.

Figure 4A:
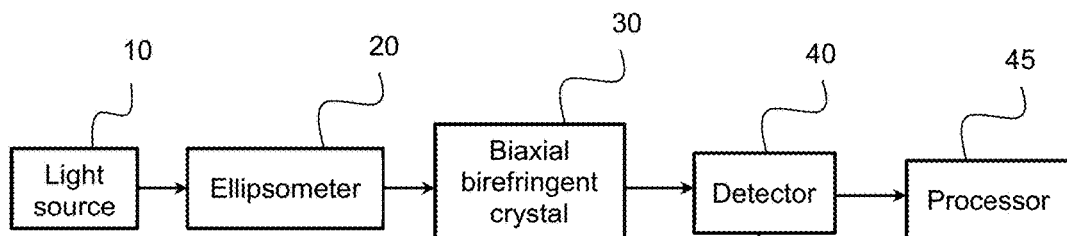
FIGS. 4a and 4b show schematically use of a biaxial crystal in conjunction with a multi-wavelength ellipsometer according to another embodiment of the present invention.
Figure 4B:
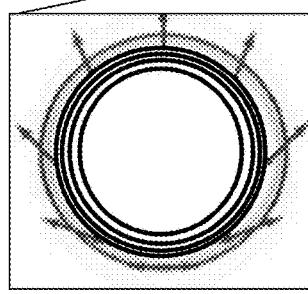

FIG. 4a shows another embodiment of the present invention in which a biaxial crystal 30 is combined with a multi-wavelength ellipsometer 20. The light source 10 of the ellipsometer is a broadband light source. In this configuration, the analyzer in the ellipsometer is avoided and the white light reflected from the object is focused and it propagates along the optic axis of the biaxial crystal 30. Behind the biaxial crystal, each wavelength of the light is transformed into a respective light ring where each point of the ring is linearly polarized with polarization plane rotating along the ring, the rings corresponding to different wavelengths being coaxial. Since the biaxial crystal 30 is dispersive and the radius of each ring depends on the crystal's length and its principal refractive indices, the respective rings of each wavelength each have a different radius, depending on the crystal's refractive index for each wavelength. Thus the broadband light is transformed into many coaxial rings of light as shown in FIG. 4b, where each point of each ring is linearly polarized with the polarization plane rotating along the ring. The rings of light are imaged either by propagation or by an optical system onto a detector array 40. Since the polarization plane of each point along the ring is rotated, it is equivalent to rotating an analyzer, thus in this configuration there no need for the rotating analyzer. Also, since the radii of the rings of each wavelength differ from each other, all of them are detected at the same time and there is no need for a spectrometer to disperse the different wavelengths.

Figure 5:
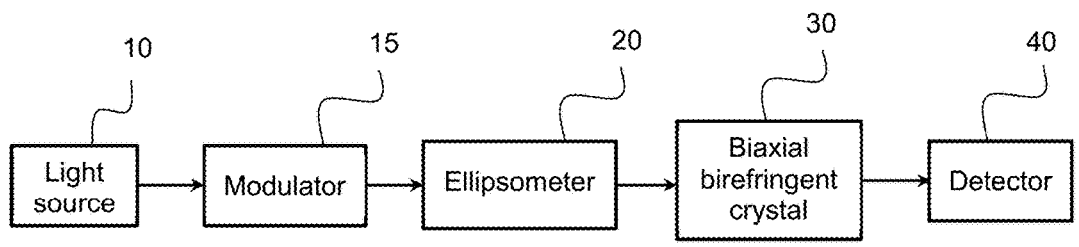
FIG. 5 shows schematically use of a biaxial crystal in conjunction with a multi-wavelength ellipsometer and a modulated light source according to another embodiment of the present invention.

FIG. 5 shows another embodiment of the present invention in which a biaxial crystal 30 is combined with a multi-wavelength ellipsometer 20 when the light source 10 is modulated by a modulator 15. The modulated light illuminates an object through the ellipsometer and the reflected light propagates through the biaxial crystal 30 to the detector array 40 to which there is coupled a processor 45 (not shown in FIG. 5) that processes the pattern imaged by the detector array 40 for obtaining an output indicating the object's optical properties.

Fourier Transform Spectrometry (FTS) utilizes a spectrometer that includes an interferometer which modulates the incoming light differently for different wavelengths due to the destructive and instructive interference. In a FTS based on a Michelson interferometer having a pair of mirrors one of which is moveable relative to the other, one of the mirrors is moved and the spectrometer actually serves as a filter with a varying cosine spectral transmission function dependent on its current optical path difference (OPD) between its mirrors. Since a filter can be located anywhere in the optical path of the light, in a FTS that utilizes a light source to illuminate an object to be analyzed, this filter can be also located just after the light source before impinging on the object. In this configuration the spectrum of the incoming light from the light source is modulated with a varying cosine function before impinging on the object. That is, by modulating the spectrum of the light source with a varying cosine function the need for using an additional spectrometer is avoided. In this case, the spectrum of the light reflected from the object is obtained by Fourier transforming its intensity function.

This embodiment describes a kind of multi wavelength ellipsometer in which there is no need for using a spectrometer or moving mirrors in the interferometer since modulating the spectrum of a broadband light source used performs an equivalent function as an interferometer. After reflecting from the object, the modulated broadband light is focused and it propagates along the optical axis of the biaxial crystal 30. Behind the biaxial crystal, the light is transformed into a light ring where each point of the ring is linearly polarized with a polarization plane rotating along the ring. The light ring is imaged either by propagation or by an optical system onto a detector array 40. Since the polarization plane of each point along the ring is rotated, it is equivalent to rotating an analyzer, therefore in this configuration there no need for the rotating analyzer. Also there is no need for a spectrometer to disperse the different wavelengths since by Fourier transforming the intensity function of the light reflected from the object, the spectrum of the reflected light can be obtained.

In still another embodiment, instead of using a modulated light source, a tunable light source such as a tunable laser is used. In this embodiment, after reflecting from the object, the light is focused and it propagates along the optical axis of the biaxial crystal 30. Behind the biaxial crystal, the light is transformed into a light ring where each point of the ring is linearly polarized with a polarization plane rotating along the ring. The light ring is imaged either by propagation or by an optical system onto a detector array 40. Since the polarization plane of each point along the ring is rotated, it is equivalent to rotating an analyzer, therefore in this configuration there no need for the rotating analyzer. Also there is no need for a spectrometer to disperse the different wavelengths since by tuning the light source, the ellipsometric data is taken at different wavelengths, one at a time.

Figure 6A:
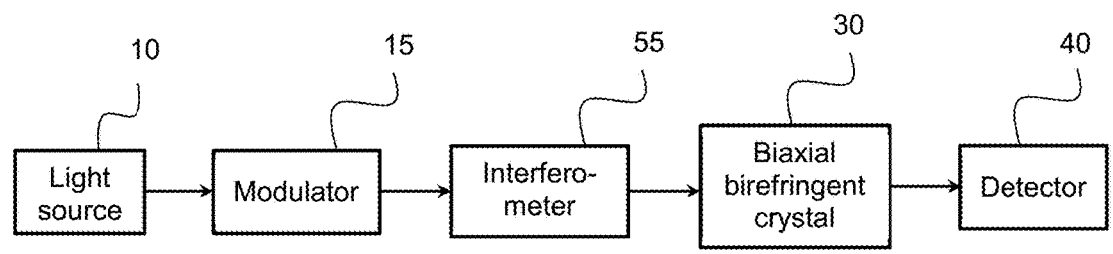
FIGS. 6a and 6b show schematically use of a biaxial crystal in conjunction with a multi-wavelength interferometer and a modulated light source according to another embodiment of the present invention.
Figure 6B:
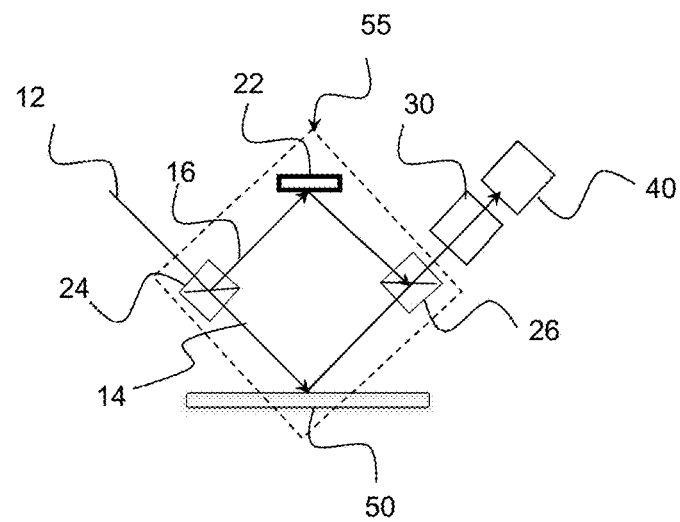

FIG. 6a shows another embodiment of the present invention in which a biaxial crystal 30 is combined with an interferometer 55 with the light source 10 which optionally may be modulated by a modulator 15. The configuration for a dual path interferometer is detailed in FIG. 6b. The beam splitter 24 splits the incoming light 12 such that one beam of light 14 illuminates the object 50 and the other beam 16 is directed to a reference mirror 22 and is used as the reference beam of the interferometer. The two beams are recombined by the beam splitter 26 and propagate through the biaxial crystal 30 to the detector array 40. Moving the reference mirror introduces a phase shift between the beams and the interference intensity varies. The complex amplitude of the light is calculated by the phase shift interferometry algorithms. The biaxial crystal transforms the light to a light ring where each point of the ring is linearly polarized with a polarization plane rotating along the ring. The light ring is imaged or detected either by propagation or by an optical system on to a detector array 40 which detects the light intensities as a function of time. Thus the complex amplitude is calculated for each polarization. In common path interferometry, the light illuminates the object and propagates through the interferometer. In the interferometer the complex amplitude of light is divided to two parts either spatially by wavefront division or by amplitude division and phase shifts are introduced between two spatial parts. The complex amplitude of the reflected light can be calculated by algorithm known in the art. The beam propagates through the biaxial crystal 30 to the detector array 40 and the complex reflectance ratio rho of light is calculated as described above. The light source may be coherent or not. If it is broadband light source it can be modulated as described above. The dispersion of the crystal may also be used to disperse the different wavelengths as described above.

The interferometer may be located in several different angles relative to the object to implement ellipsometry. Alternatively, the interferometer may be located normal or in several different angles to the object to implement reflectometry. In ellipsometry, the complex reflectance ratio rho of light is attained by dividing a complex amplitude of one polarization by the complex amplitude of its normal polarization. This can be done for every two normal polarizations to increase the accuracy. In reflectometry, the complex amplitude attained for each polarization can be compared to a calculated complex amplitude attained by a simulated amplitude. In small features in the object a form birefringence may be obtained and such comparison can increase the accuracy of the measurements.

The light source may also be located normal to the object or in several different angles relative to the object and it may be modulated as described above. The interferometer may be any kind of interferometer, Time Domain Optical Coherence Tomography (OCT), Fourier Domain OCT, Swept Source OCT, Dual Beam OCT, etc. This kind of Ellipsometry or Reflectometry is not sensitive to vibrations since the two polarizations suffer from the same vibrations and cancel each other's vibrations. In all cases described above the birefringent crystal may be omitted.

It should also be understood that in the arrangements shown in FIGS. 3, 4 and 5 the ellipsometer can be replaced by a reflectometer and the computations are then carried out for reflectometry as described above.

In particular it should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. An apparatus comprising:
   a tunable monochromatic light source configured to illuminate at least one point of an object;
   a polarizer configured to be disposed between the light source and the object, the polarizer being configured to polarize light from the light source;
   a biaxial birefringent crystal (a) positioned to intercept a beam of light reflected from the object, (b) positioned to propagate the beam along an optical axis of the crystal, and (c) configured to transform the beam of reflected light into a ring of light, (i) each point of the ring of light having a different polarization plane, and (ii) a diameter of the ring of light being different for different respective wavelengths of the light from the tunable monochromatic light source; and
   a detector array configured to simultaneously detect respective points along the ring of light for each of a plurality of wavelengths of the tunable monochromatic light source, such that images are acquired by the detector array at different wavelengths, one at a time.

2. The apparatus according to claim 1:
   further comprising an interferometer positioned such that, when the light source is activated, (a) light from the light source enters the interferometer and is split into two beams of light, a first one of the beams of light illuminating the object and a second one of the beams of the light being directed to a reference mirror, and (b) after respectively reflecting off the reference mirror and the object the first and second beams of light are recombined into a single reflected beam of light, and
   wherein the biaxial birefringent crystal is positioned to intercept the recombined single reflected beam of light.

3. The apparatus according to claim 2, wherein the interferometer comprises a Time Domain Optical Coherence Tomography interferometer.

4. The apparatus according to claim 2, wherein the interferometer comprises a Fourier Domain Optical Coherence Tomography interferometer.

5. The apparatus according to claim 2, wherein the interferometer comprises a Swept Source Optical Coherence Tomography interferometer.

6. The apparatus according to claim 2, wherein the interferometer comprises a Dual Beam Optical Coherence Tomography interferometer.

7. A method comprising:

determining at least one optical property of at least a portion of an object by:

illuminating at least one point of the object with light from a tunable monochromatic light source;

directing light reflected from the object on to a biaxial birefringent crystal, such that light reflected from the object is propagated along an optical axis of the crystal so as to transform the reflected light to a ring of light, (i) each point of the ring of light having a different polarization plane and (ii) a diameter of the ring of light being different for different respective wavelengths of the light from the tunable monochromatic light source;

spectrally tuning the light source to generate light at a plurality of wavelengths;

simultaneously detecting respective points of the ring of light for different respective wavelengths of the reflected light, one wavelength at a time; and processing the detected respective points to determine at least one optical property of the object.

8. The method according to claim 7, wherein:

illuminating comprises directing the light from the tunable monochromatic light source into an interferometer, such that (a) light is split into two beams of light, a first one of the beams of light illuminating the object and a second one of the beams of light being directed to a reference mirror, and (b) after respectively reflecting off the reference mirror and the object, the first and second beams of light are recombined into a single reflected beam of light, and directing light reflected from the object onto the biaxial birefringent crystal comprises directing the recombined single reflected beam of light onto the biaxial birefringent crystal.

9. The method according to claim 8, wherein directing the light from the tunable monochromatic light source into the interferometer comprises directing the light from the tunable monochromatic light source in to a Time Domain Optical Coherence Tomography interferometer.

10. The method according to claim 8, wherein directing the light from the tunable monochromatic light source into the interferometer comprises directing the light from the tunable monochromatic light source in to a Fourier Domain Optical Coherence Tomography interferometer.

11. The method according to claim 8, wherein directing the light from the tunable monochromatic light source into the interferometer comprises directing the light from the tunable monochromatic light source in to a Swept Source Optical Coherence Tomography interferometer.

12. The method according to claim 8, wherein directing the light from the tunable monochromatic light source into the interferometer comprises directing the light from the tunable monochromatic light source in to a Dual Beam Optical Coherence Tomography interferometer.

* * * * *